US00PP35942P2

(12) United States Plant Patent
Glawe et al.

(10) Patent No.: US PP35,942 P2
(45) Date of Patent: Jul. 2, 2024

(54) ***PELARGONIUM* PLANT NAMED 'KLEPZ22686'**

(50) Latin Name: *Pelargonium zonale*
Varietal Denomination: KLEPZ22686

(71) Applicant: KLEMM + SOHN GMBH & CO. KG, Stuttgart (DE)

(72) Inventors: Martin Glawe, Stuttgart (DE); Nina Neu, Weissach im Tal (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/320,193

(22) Filed: May 18, 2023

(51) Int. Cl.
*A01H 5/02* (2018.01)
*A01H 6/42* (2018.01)

(52) U.S. Cl.
USPC ..... Plt./329

(58) Field of Classification Search
USPC ..... Plt./329, 328
CPC ... A01H 5/02; A01H 5/00; A01H 6/42; A01H 6/425
See application file for complete search history.

(56) References Cited

U.S. PATENT DOCUMENTS

PP19,202 P2 * 9/2008 Michalik ..... A01H 6/42 Plt./329

OTHER PUBLICATIONS

Pac Elsner for Pac Marena, retrieved on Aug. 29, 2023 at https://www.pac-elsner.com/en/detail/show/pac-marena.html, one page. (Year: 2023).*

* cited by examiner

*Primary Examiner* — June Hwu
(74) *Attorney, Agent, or Firm* — Weatherly IP Solutions, LLC; James M. Weatherly

(57) ABSTRACT

A new *Pelargonium* plant particularly distinguished by a dark magenta flower color; small, dark green leaves; and strong zonation, is disclosed.

1 Drawing Sheet

Genus and species: *Pelargonium zonale.*
Variety denomination: 'KLEPZ22686'.

BACKGROUND OF THE NEW PLANT

The present invention comprises a new and distinct variety of *Pelargonium*, botanically known as *Pelargonium zonale* and hereinafter referred to by the variety name 'KLEPZ22686'. 'KLEPZ22686' originated from a controlled cross in August 2017 in Nairobi, Kenya between the proprietary female *Pelargonium* variety 'KLE03105' (unpatented) and the proprietary male *Pelargonium* variety 'PZ-2013-0158' (unpatented).

Seeds from the controlled-cross were obtained. The seeds were sown and plants were grown for evaluation. A single plant was selected in June 2018 and subsequently named 'KLEPZ22686'. In July 2018 'KLEPZ22686' was first vegetatively propagated by vegetative stem cuttings in Stuttgart, Germany. 'KLEPZ22686' was found to reproduce true to type in successive generations of asexual propagation via stem cuttings in Stuttgart, Germany.

SUMMARY

The following are the most outstanding and distinguishing characteristics of this new variety when grown under normal horticultural practices in Latina, Italy.

1. Dark magenta flower color;
2. Small, dark green leaves; and
3. Strong zonation.

DESCRIPTION OF THE PHOTOGRAPH

This new *Pelargonium* plant is illustrated by the accompanying photograph which shows an overall view of the plant in a pot. The photograph is of an approximately 13-week-old plant grown outdoors in Stuttgart, Germany, in April 2021. The colors shown are as true as can be reasonably obtained by conventional photographic procedures.

DESCRIPTION OF THE NEW VARIETY

The following detailed descriptions set forth the distinctive characteristics of 'KLEPZ22686'. Data was collected on 19-week-old plants in Latina, Italy under greenhouse conditions in April 2023. Color references are to The R.H.S. Colour Chart of The Royal Horticultural Society of London (R.H.S.), 5$^{th}$ edition (2007).

Classification:
*Family.*—Geraniaceae.
*Botanical.*—*Pelargonium zonale.*
*Common.*—*Pelargonium.*
*Designation.*—'KLEPZ22686'.

Parentage:
*Female parent.*—'KLE03105' (unpatented).
*Male parent.*—'PZ-2013-0158' (unpatented).

Plant:
*Form.*—Bushy.
*Habit.*—Upright.

*Height* (*from top of soil*).—20.5 cm.
*Width* (*horizontal plant diameter*).—29.5 cm.
*Natural flowering season*.—March to October.
*Propagation type*.—Vegetative.
*Time to produce a finished flowering plant*.—12 weeks.
*Time to initiate and develop roots*.—4 weeks.
*Root description*.—Fine, dense, white (RHS N155C).

Stems:
*Quantity of stems per plant*.—5 to 6.
*Color*.—RHS 146B.
*Surface texture*.—Pubescent.
*Stem form*.—Round.
*Diameter* .—0.9 cm.
*Length*.—7.0 cm to 8.0 cm.
*Internode length*.—2.5 cm.
*Anthocyanin*.—Absent.

Leaves:
*Arrangement*.—Alternate.
*Shape*.—Reniform.
*Apex*.—Round.
*Base*.—Open.
*Margin*.—Crenate.
*Surface texture both surfaces*.—Pubescent.
*Length*.—5.0 cm.
*Width*.—6.5 cm.
*Color*.—Upper surface: RHS N137A. Lower surface: RHS N137C.
*Zonation*.—Strong, middle of leaf area, 0.7 cm width.
*Zonation color*.—RHS 203B.
*Depth of sinus*.—0.5 cm.
*Petiole*.—Length: 5.6 cm. Diameter: 0.2 cm. Color: RHS 146B. Strength: Weak.
*Venation pattern*.—Palmate.
*Venation color*.—Upper surface: RHS N137A. Lower surface: RHS 146B.

Inflorescence:
*Flower type*.—Double flower.
*Lastingness of flowers on the plant*.—6 to 8 days.
*Umbels*.—Quantity of umbels per plant: 5 to 7. Length: 9.0 cm. Diameter: 10.3 cm.
*Individual florets of the umbel*.—Quantity of florets per umbel: 8 to 10. Depth: 2.4 cm. Diameter: 4.8 cm.
*Fragrance*.—Absent.

Flower buds:
*Cluster shape*.—Round.
*Cluster size*.—Length: 1.8 cm. Width: 1.9 cm.
*Surface texture*.—Pubescent.
*Bud*.—Height: 0.8 cm. Width: 0.5 cm. Shape: Round. Apex: Acute. Base: Obtuse. Margin: Entire. Color: RHS 146A.

Petals:
*Quantity per flower*.—7 to 8.
*Shape*.—Spatulate.
*Apex*.—Round.
*Base*.—Obtuse.
*Margin*.—Entire.
*Length*.—3.0 cm.
*Width*.—2.5 cm.
*Surface texture*.—Upper surface: Smooth. Lower surface: Smooth.
*Color of lobes*.—Upper lobes: Upper surface: RHS N66A. Lower surface: RHS N66B. Lower lobes: Upper surface: RHS N66A. Lower surface: RHS N66B.

Petaloids:
*Quantity per flower*.—3 to 7.
*Shape*.—Crippled, different shapes from drepanium to spatulate to linear to flame like.
*Apex*.—Round or acute.
*Base*.—Obtuse.
*Margin*.—Entire.
*Length*.—0.8 cm to 1.8 cm.
*Width*.—0.3 cm to 1.0 cm.
*Surface texture*.—Upper surface: Smooth. Lower surface: Smooth.
*Color*.—Upper surface: RHS N66A. Lower surface: RHS N66B.
*Markings*.—Absent.

Sepals:
*Number per flower*.—5.
*Shape*.—Elliptic.
*Apex*.—Acute.
*Base*.—Obtuse.
*Margin*.—Entire.
*Reflexing*.—Absent.
*Surface texture*.—Upper surface: Smooth. Lower surface: Pubescent.
*Color*.—Upper surface: RHS 146A with RHS 183A at the base. Lower surface: RHS 146A with RHS 183A at the base.
*Length*.—1.4 cm.
*Width*.—0.5 cm.

Pedicel:
*Length*.—4.2 cm.
*Diameter*.—0.2 cm.
*Color*.—RHS 183A.
*Surface texture*.—Pubescent.
*Strength*.—Weak.
*Swelling*.—Not present.

Peduncle:
*Length*.—9.2 cm.
*Diameter*.—0.4 cm.
*Color*.—RHS 146B with sometimes RHS 187A on some areas.
*Texture*.—Pubescent.
*Strength*.—Medium.

Reproductive organs:
*Stamens*.—Quantity per flower: 3 to 5. Anther length: 0.3 cm. Filament length: 0.8 cm. Filament color: RHS N155A at the base, rest has RHS 67C. Pollen amount: Few. Pollen color: RHS 169A.
*Pistils*.—Number: 1. Stigma color: RHS 185A. Style length: 0.1 cm. Style color: RHS 185A. Ovary arrangement: Central. Ovary color: RHS 187A. Ovary diameter: 0.2 cm. Ovary length: 0.6 cm. Ovary Texture: Pubescent.

Fruit and seed set: None observed.

Disease and pest/insect resistance: None observed.

COMPARISON WITH PARENTAL LINES AND KNOWN VARIETY

'KLEPZ22686' is distinguished from its parents as described in Table 1.

TABLE 1

| Comparison with Parental Lines | | | |
|---|---|---|---|
| Characteristic | 'KLEPZ22686' | Female parent | Male parent |
| Flower Color | Dark magenta | Orange red | Purple |
| Zonation | Strong | Very strong | Medium |
| Leaf Color | Dark green | Green | Dark green |

'KLEPZ22686' can be compared to the commercial variety 'Pacmar' (U.S. Plant Pat. No. 19,202. Differences between the two varieties are described in Table 2:

TABLE 2

| Comparison with Similar Variety | | |
|---|---|---|
| Characteristic | 'KLEPZ22686' | 'Pacmar' |
| Leaf Size | Small | Medium to big |
| Flower Color | Dark magenta | Magenta pink |
| Zonation | Strong | Weak |

We claim:

1. A new and distinct cultivar of *Pelargonium* Plant Named 'KLEPZ22686' as described and illustrated herein.

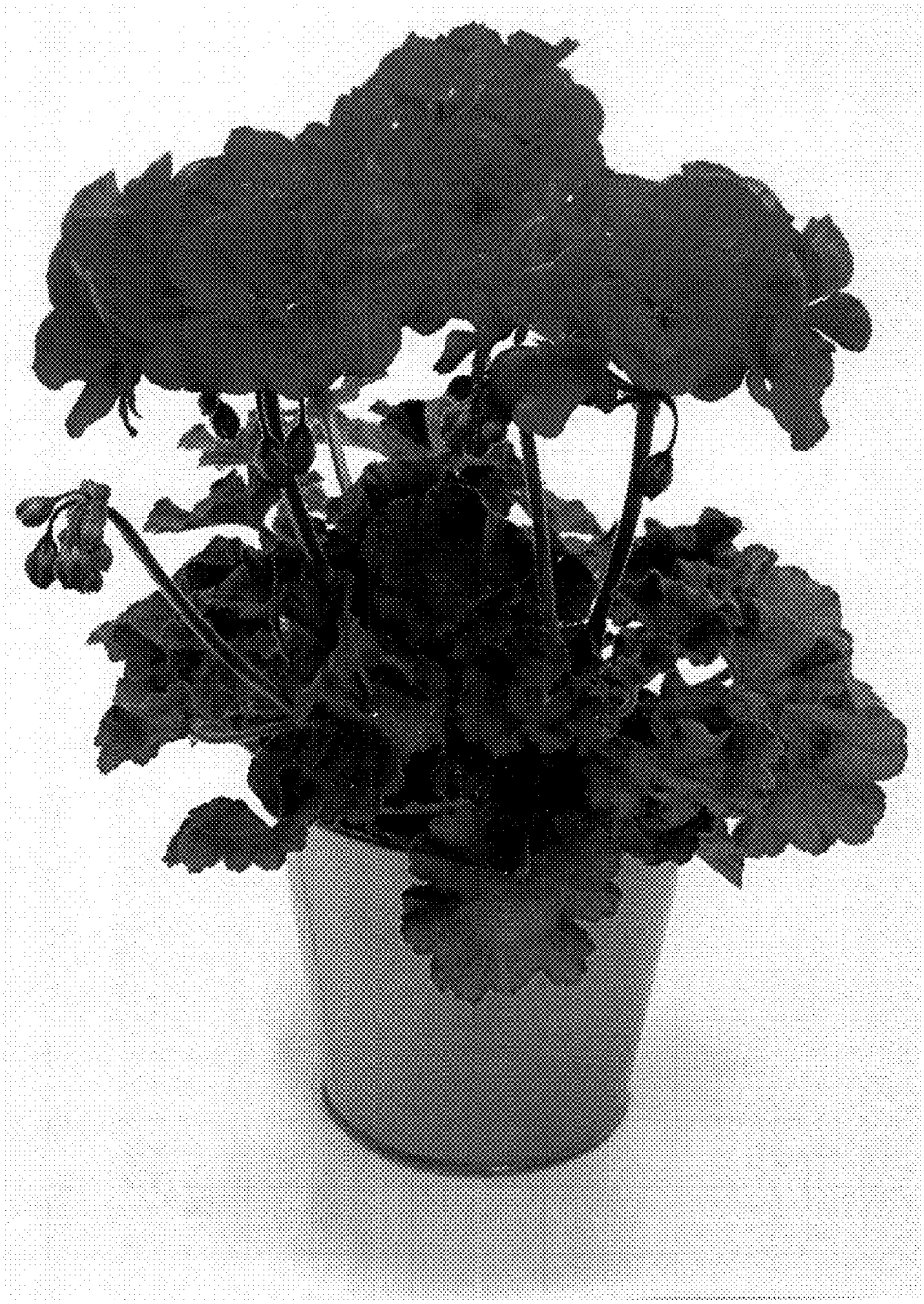

* * * * *